(12) United States Patent
Dominguez Holguin

(10) Patent No.: US 10,307,795 B2
(45) Date of Patent: Jun. 4, 2019

(54) SCALABLE SYSTEMS AND METHODS FOR CLASSIFYING TEXTILE SAMPLES

(71) Applicant: Jessica Schreiber Dominguez Holguin, New York, NY (US)

(72) Inventor: Jessica Schreiber Dominguez Holguin, New York, NY (US)

(73) Assignee: FABSCRAP, Inc., New York, NY (US)

( * ) Notice: Subject to any disclaimer, the term of this patent is extended or adjusted under 35 U.S.C. 154(b) by 0 days.

(21) Appl. No.: 15/587,206

(22) Filed: May 4, 2017

(65) Prior Publication Data

US 2017/0320103 A1     Nov. 9, 2017

Related U.S. Application Data

(60) Provisional application No. 62/331,787, filed on May 4, 2016.

(51) Int. Cl.
*B07C 5/34*     (2006.01)
*G01N 3/26*     (2006.01)

(52) U.S. Cl.
CPC .............. *B07C 5/34* (2013.01); *G01N 3/26* (2013.01); *G01N 2203/0017* (2013.01); *G01N 2203/0067* (2013.01)

(58) Field of Classification Search
CPC ........... B07C 5/34; B07C 5/342; B07C 5/344; G01N 3/08; G01N 3/22; G01N 3/24; G01N 3/26; G01N 2203/0016; G01N 2203/0017; G01N 2203/0021; G01N 2203/0026; G01N 2203/0067
See application file for complete search history.

(56) References Cited

U.S. PATENT DOCUMENTS

| | | | | | |
|---|---|---|---|---|---|
| 2,967,947 | A | * | 1/1961 | Flook, Jr. ............... | D02H 13/00 250/207 |
| 3,540,923 | A | * | 11/1970 | Rozek ................. | D06M 13/127 427/389 |
| 3,574,409 | A | * | 4/1971 | Furstenberg ........... | B65G 53/06 406/120 |
| 3,835,697 | A | * | 9/1974 | Schneider ................ | G01N 3/56 73/159 |
| 3,987,665 | A | * | 10/1976 | Hansen .................. | G01N 29/12 73/159 |
| 4,148,218 | A | * | 4/1979 | Knowles .............. | G01M 11/088 65/486 |
| 4,208,920 | A | * | 6/1980 | Graham ................... | G01N 3/16 73/828 |

(Continued)

FOREIGN PATENT DOCUMENTS

| | | | | |
|---|---|---|---|---|
| WO | WO-9843055 A1 | * | 10/1998 | ............... G01L 5/10 |
| WO | WO-2007026143 A1 | * | 3/2007 | ............... G01N 3/08 |

*Primary Examiner* — Joseph C Rodriguez
(74) *Attorney, Agent, or Firm* — Brownstein Hyatt Farber Schreck, LLP

(57) ABSTRACT

Systems and methods for classifying and sorting textile samples. A textile identification system may be configured to manipulate a textile sample in a manner that reveals a textile characteristic. For example, an elastic property of the textile sample is revealed by stretching or twisting the sample. The textile sample may be classified based on the textile characteristic. The textile sample may be sorted based on the classification.

20 Claims, 11 Drawing Sheets

(56) References Cited

U.S. PATENT DOCUMENTS

| | | | | |
|---|---|---|---|---|
| 5,050,437 A * | 9/1991 | Etter | G01N 3/08 | 73/830 |
| 5,167,150 A * | 12/1992 | Shofner | G01N 3/08 | 356/429 |
| 5,178,008 A * | 1/1993 | Aemmer | G01N 33/365 | 700/144 |
| 5,203,206 A * | 4/1993 | Shofner | G01N 3/08 | 73/160 |
| 5,596,901 A * | 1/1997 | Gloor | G01B 11/08 | 73/159 |
| 5,813,277 A * | 9/1998 | Schmidt | G01N 33/367 | 73/12.13 |
| 5,846,030 A * | 12/1998 | Beard | B65G 51/02 | 406/1 |
| 6,318,166 B1 * | 11/2001 | Roos | G01N 3/08 | 73/160 |
| 6,487,902 B1 * | 12/2002 | Ghosh | G01L 5/045 | 73/159 |
| 6,499,356 B1 * | 12/2002 | Flaud | G01N 3/08 | 73/831 |
| 6,609,408 B2 * | 8/2003 | Chen | G01N 3/08 | 702/34 |
| 6,741,726 B1 * | 5/2004 | Nevel | G01B 11/105 | 356/429 |
| 6,860,148 B2 * | 3/2005 | Kossuth | G01N 19/02 | 73/159 |
| 7,357,982 B2 * | 4/2008 | Abe | D01F 6/74 | 428/364 |
| 7,375,806 B2 * | 5/2008 | Daul | G01N 21/86 | 356/236 |
| 7,509,874 B2 * | 3/2009 | Kuenzli | D06H 3/16 | 223/75 |
| 7,703,332 B2 * | 4/2010 | Watkins | G01N 3/08 | 73/159 |
| 8,170,842 B2 * | 5/2012 | Ognjanovic | G06F 17/5018 | 156/229 |
| 8,190,551 B2 * | 5/2012 | Busch | G01N 3/359 | 706/54 |
| 9,869,620 B2 * | 1/2018 | Righettini | G01N 3/08 | |

* cited by examiner

SCALABLE SYSTEMS AND METHODS FOR CLASSIFYING TEXTILE SAMPLES

CROSS-REFERENCE TO RELATED APPLICATION(S)

This application is a nonprovisional patent application of and claims the benefit of U.S. Provisional Patent Application No. 62/331,787, filed May 4, 2016 and titled "Scalable Systems and Methods for Classifying Textile Samples," the disclosure of which is hereby incorporated herein by reference in its entirety.

TECHNICAL FIELD

Embodiments described herein are directed to systems and methods for classifying like materials and, in particular, to scalable systems and methods for classifying textile samples.

BACKGROUND

Unusable or unwanted sections of natural or synthetic material are often discarded as waste and not processed for reuse, repurposing, or recycling. These sections of material may accumulate over time. For example, scrap material may accumulate in the course of producing consumer or commercial goods. In another example, used consumer or commercial goods may accumulate after being discarded upon becoming unsuitable for an original or intended purpose (e.g., ripped, tattered, soiled, or threadbare goods).

Typically, although such accumulated material may be recyclable or reusable, it is often diverted to, and disposed of, in landfills. In many cases, this may be due to the inconvenience and expense associated with sorting a high volume of accumulated material into groups of like material in preparation for material-specific reuse, repurposing, or recycling. In particular, conventional systems and methods for sorting like materials may be unable to classify a wide variety of materials, may require input from one or more well-trained equipment operators, may be time consuming to operate, and/or may be prohibitively expensive to operate and maintain.

SUMMARY

Embodiments described herein generally reference systems and methods for sorting textile samples into groups based on textile types in a scalable manner. Once sorted, groups of like materials that are collected using systems or methods described herein may be packaged, prepared, or otherwise processed for reuse, repurposing, or recycling. In other cases, such groups of like materials may be processed for efficient and responsible disposal by incineration, disintegration, biodegradation, or any other suitable material-specific or material-appropriate disposal method.

Certain embodiments described herein reference a method of classifying a textile sample by manipulating a textile sample in a manner that reveals or corresponds to one or more properties of that sample. The property can be used to classify the sample as one of a subset of textile types. For example, the textile sample can be manipulated by stretching, ripping, folding, twisting, vibrating, or by using any other suitable method. Based on one or more properties of the manipulation and/or one or more physical properties of the textile sample (e.g., color, weave pattern, original source, weight, combustion temperature, combustion spectral pattern, combustion spectral pattern, and so on), the textile sample can be identified and/or classified. The manipulation may be non-destructive, destructive, or partially destructive.

More particularly, in one embodiment, a sample of unknown material is selected. The sample may be stretched along a selected axis with a given amount of force. Various properties of the sample may be measured or monitored while the sample is stretched. These properties and/or changes in these properties may be used to classify the sample.

For example, a color of the sample may be monitored while the sample is stretched. The sample may be identified based on an amount of color change, if any, exhibited by the sample before, during, and/or after sample is stretched.

In another example, a length of the sample may be monitored while the sample is stretched. The sample may be identified based on an amount of change in the length, if any, exhibited by the sample before, during, and/or after the sample is stretched.

In another example, a weave pattern of the sample may be monitored while the sample is stretched. The sample may be identified based on an amount of change in the weave pattern, if any, exhibited by the sample before, during, and/or after the sample is stretched. In other cases, the sample may be stretched multiple times. In some cases, the sample may be stretched along more than one axis.

In another embodiment, another sample of unknown material is selected. The sample may be stretched along a selected axis until the sample rips. As with other embodiments described herein, various properties of the sample may be measured or monitored while the sample is ripped. These properties and/or changes in these properties may be used to classify the sample.

For example, a color of the sample may be monitored while the sample rips. The sample may be identified based on an amount of color change, if any, exhibited by the sample before, during, and/or after sample rips.

In another example, a length of the sample may be monitored while the sample is ripped. The sample may be identified based on an amount of change in the length, if any, exhibited by the sample before, during, and/or after the sample rips.

In another example, sound generated by the sample may be monitored while the sample is ripped. The sample may be identified based on an amount of change in the sound (e.g., change in volume, frequency spectrum, duration, and so on), if any, generated by the sample before, during, and/or after the sample rips.

In yet another example, an amount of force required to cause the sample to rip may be monitored while the sample rips. In some cases, one or more characteristics of the rip itself may be used to classify the sample. These characteristics include, but are not limited to, path of the rip, an amount of force required to initiate the rip, an amount of force required to continue the rip, an amount or spectrum of infrared energy emitted from the sample during the rip, an amount of fraying of the sample as a result of the rip, and so on.

BRIEF DESCRIPTION OF THE FIGURES

Reference will now be made to representative embodiments illustrated in the accompanying figures. It should be understood that the following descriptions are not intended to limit the embodiments to one preferred embodiment. To the contrary, it is intended to cover alternatives, modifications, and equivalents as may be included within the spirit and scope of the described embodiments as defined by the appended claims.

The use of the same or similar reference numerals in different figures indicates similar, related, or identical items.

Figure 1:
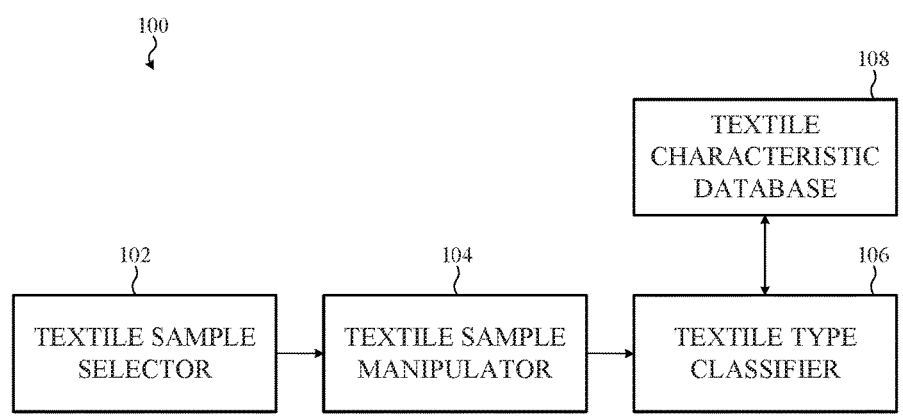
FIG. 1 depicts a simplified system diagram of a textile identification system that may operate in accordance with methods described herein.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Embodiments described herein generally reference scalable systems and methods for classifying and/or categorizing material samples. Such systems may be suitable for high-volume sorting and classification of material samples. Material samples such as described herein can be of any suitable size, shape, weight, density, and so on.

For simplicity of description, many embodiments described herein reference systems and methods for sorting and identifying textile samples, but it may be appreciated that any number of suitable materials may be sorted, categorized, or otherwise identified using the systems and methods described herein. For example, suitable materials that can be sorted, categorized, and/or otherwise sorted using the techniques and methods described herein include, but may not be limited to: organic materials (e.g., wood, natural fibers, and so on), synthetic materials (e.g., polymers, rubbers, and so on), metals, glass, ceramics, multi-layered materials, single-layer materials, minerals, plastics, manufactured materials (e.g., fiberboard, fiberglass, particleboard, and so on), hollow materials, solid materials, structured materials (e.g., corrugated cardboard), and so on.

Once classified using a system and/or method such as described herein, a textile sample may be sorted into like groups and processed for material-specific or material-appropriate reuse, repurposing, or recycling. In other cases, groups of like materials may be processed for efficient and responsible disposal by incineration, disintegration, biodegradation, or any other suitable material-specific, or material-appropriate, disposal method. As a result the systems and methods described herein, accumulation of textile materials in landfills may be moderated.

More specifically, embodiments described herein reference various methods of classifying and/or categorizing a textile sample in a time-efficient, cost-efficient, and scalable manner by manipulating the textile sample in a manner that reveals, or corresponds to, one or more properties or characteristics of that sample (e.g., a "textile characteristic"). The manipulation may be non-destructive, destructive, or partially destructive. For example, stretching the sample may reveal a modulus of elasticity (e.g., Young's modulus) of the sample. In some cases, a single sample may be stretched along more than one axis in order to reveal more than one textile characteristic that corresponds to more than one modulus of elasticity. In another example, ripping the sample may reveal an acoustic property of the sample. In yet another example, combusting the sample may reveal a chemical property of the sample.

After determining one or more textile characteristics and/or one or more physical properties of the textile sample (e.g., color, weave pattern, original source, weight, and so on), the textile sample can be classified as a particular textile type. In other cases, the textile sample can be assigned or classified as more than one textile type. The textile type(s) may correspond to a material type (e.g., synthetic, natural, hybrid, and so on), a recyclability type (e.g., highly recyclable, recyclable, not recyclable, and so on), a material description (e.g., cotton, leather, nylon, acetate, wool, blended fibers, polyester, bamboo, linen, silk, satin, tweed, felt, hemp, and so on), a market demand type (e.g., a rare material, a common material, a popular material, an unpopular material), and so on.

In many cases, the textile type(s) can be determined by comparing the one or more textile characteristics and/or one or more physical properties of the textile sample (collectively or independently, "textile sample data") to a database of textile characteristics. Any suitable matching or classification technique can be used to compare textile sample data to data contained in a textile characteristic database including, but not limited to, neural network classification techniques, linear classification techniques, support vector machine techniques, quadratic classification techniques, decision tree techniques, chemometric modeling and classification, operator-assisted classification techniques, and so on.

Once assigned and/or classified as a particular textile type (or multiple textile types), the textile sample may be sorted with other similarly-classified textile samples. In other words, the textile sample may be grouped with other like materials. After the textile sample is grouped with other like materials, group of materials may be packaged and/or processed for reuse, repurposing, or recycling.

In many cases, a group of textile samples may be sorted based on a textile type of a single textile sample selected from that group. For example, it may be known that a group of textile samples all have the same textile type or textile types because that group of textile samples were received from the same source.

It is with respect to these and other embodiments that FIGS. 1-10 are provided. However, those skilled in the art will readily appreciate that the detailed description given herein with respect to these figures is for explanatory purposes only and should not be construed as limiting.

FIG. 1 depicts a simplified system diagram of a textile identification system that may operate in accordance with methods described herein. The textile identification system 100 can be implemented in any number of suitable ways however, in many embodiments, the textile identification system 100 includes a textile sample selector 102, a textile sample manipulator 104, and a textile type classifier 106. In many cases, the textile type classifier 106 is in communication with a textile characteristic database 108.

The textile sample selector 102 of the textile identification system 100 is configured to select a textile sample from a group of textile samples. The group of textile samples may be a homogenous group of textile samples, or may be a random group of textile samples.

The textile sample selector 102 may be configured to select a textile sample from the group based on, without limitation, a size of the textile sample relative to other textile samples of the group, a color of the textile sample relative to other textile samples of the group, a length of the textile sample relative to other textile samples of the group and so on. In other embodiments, the textile sample selector 102 may select any textile sample of the group of textile samples.

The textile sample selector 102 can be implemented in any number of suitable ways. For example, the textile sample selector 102 may be a pick-and-place machine, a grappling arm, a vacuum pick-up tool, a gated or indexing conveyor, and so on. In other embodiments, the textile sample selector 102 can be implemented in another manner. For example, the textile sample selector 102 may be assisted by an operator. In some cases, an operator may select a textile sample; the textile sample selector 102 receives the selected sample directly from the operator.

In many embodiments, the textile sample selector 102 broadly includes, or is in communication with, one or more of a processor, a memory, a power supply, one or more sensors, one or more communication interfaces, one or more data connectors, one or more power connectors, one or more input/output devices (such as a speaker, a rotary input device, a microphone, an on/off button), and so on.

In many embodiments, the textile sample selector 102 can also include a vision system with one or more cameras. The vision system may be used by the textile sample selector 102 to determine which textile sample of the group of textile samples should be selected. The vision system may be an infrared camera system, a visible light camera system, a combination infrared and visible light camera system, or can be any other suitable camera system or combination of camera systems. In some cases, the vision system may include one or more depth-of-field sensors and/or three-dimensional imaging or processing modules.

The textile sample manipulator 104 of the textile identification system 100 is configured to manipulate the selected textile sample in a manner that reveals, or corresponds to, a textile characteristic of the textile sample. More specifically, the textile sample manipulator 104 is configured to obtain textile sample data that can be correlated to a textile characteristic by, in one example, the textile type classifier 106.

The textile sample manipulator 104 can manipulate the textile sample in any number of suitable ways including, but not limited to: stretching; ripping; folding; twisting; vibrating; shearing; chemically disintegrating; dissolving; saturating with a chemical or fluid; freezing; heating; exposing to frequencies of light or sound; exposing to magnetic or electric fields; and so on. In many embodiments, the textile sample manipulator 104 is configured to manipulate the textile sample in more than one manner.

The textile characteristic(s) revealed by the manipulation(s) may be, without limitation: length; width; thickness; number of layers; color; weave pattern; selvage location; selvage type; seam type; weave technique; weave pattern; weave material; weft material; modulus of elasticity; propensity to tear; opacity; optical transmittance, absorption, or reflectivity; ultraviolet reflectivity, absorption, or transmittance; electrostatic adhesion; elastic recovery; tenacity; and so on.

The textile sample manipulator 104 can include, or may be in communication with, any number of suitable components or sensors such as one or more of a processor, a memory, a power supply, one or more sensors, one or more communication interfaces, one or more data connectors, one or more power connectors, one or more input/output devices, such as a speaker, a rotary input device, a microphone, an on/off button, and so on. The textile sample manipulator 104 can include sensors such as, but not limited to: force sensors, strain sensors, light sensors, acoustic sensors, temperature sensors, camera systems, thermal imaging systems, gas chromatography systems, x-ray spectroscopy systems, near infrared spectroscopy systems, combustion systems, chemical delivery and/or collection systems, and so on.

In one particular example, the textile sample manipulator 104 can be configured to obtain textile sample data related to an elasticity of the textile sample. In one example, the textile sample manipulator 104 is configured to grasp the textile sample along an axis, such as a length or a width. Thereafter, the textile sample manipulator 104 may be configured to stretch the textile sample with a selected or pre-determined amount of force. During the stretching operation, various properties of the textile sample can be monitored for changes and recorded as textile sample data such as, but not limited to: length, width, shape, color, resistance to stretching, and so on. In further embodiments, any sounds emitted from the textile sample during the stretch may also be monitored and/or recorded by an acoustic sensor. In still further embodiments, a temperature of the textile sample during the stretch may also be monitored and/or recorded.

In other cases, the amount of force applied by the textile sample manipulator 104 to the textile sample can vary. For example, the textile sample manipulator 104 may apply a force having a magnitude that increases linearly, exponentially, logarithmically, or arbitrarily. In other cases, the textile sample manipulator 104 may be configured to apply a force having a magnitude that increases and decreases over time (e.g., sinusoidal force curve). As such, it may be appreciated that the textile sample manipulator 104 can apply a force, or more than one force, to the textile sample in any number of suitable ways, one or more times.

In some embodiments, after applying the pre-determined amount of force, the textile sample manipulator 104 releases the textile sample. Thereafter, the textile sample manipulator 104 may monitor any shape recovery exhibited by the textile sample. More specifically, the textile sample manipulator 104 can determine whether the textile sample returned to its original size and shape, whether the textile sample recovered to a size and shape that is different from its original size and shape, or whether the textile sample did not recover. The amount and degree of recovery, if any, may also be recorded as textile sample data.

In another example, the textile sample manipulator 104 is configured to obtain one or more textile sample data related to an elasticity of the textile sample in another manner. As with embodiments described above, the textile sample manipulator 104 is configured to grasp the textile sample along an axis, such as a length or a width. In one example, the textile sample manipulator 104 is configured to grasp the textile sample along an axis forty-five degrees offset the weave pattern. This axis is referred to as the stretch axis. In addition, the textile sample manipulator 104 is configured to grasp the textile sample along an axis that is perpendicular to the stretch axis. This axis is referred to as the resistance axis.

Thereafter, the textile sample manipulator 104 is configured to stretch the textile sample with a selected or pre-determined amount of force along the stretch axis. This operation can cause the resistance axis to exert a force that pulls toward the stretch axis. The textile sample manipulator 104 is configured to measure this resistance during the stretch, recording the resistance as textile sample data.

As with the embodiment described above, during the stretching operation, various properties of the textile sample can be monitored for changes and recorded as textile sample data such as length along the stretch axis or resistance axis.

In another embodiment, the textile sample manipulator 104 may be configured to rip the textile sample or a portion of the textile sample. The textile sample manipulator 104 may perform this operation in any number of suitable ways. Textile sample data can be recorded such as, but not limited to: whether the textile sample ripped; the direction and propagation pattern of the rip of the textile sample; sounds emitted from the textile sample upon ripping; change in temperature of the textile sample upon ripping; and so on.

In another embodiment, the textile sample manipulator 104 may be configured to attempt to combust the textile sample or a portion of the textile sample. The textile sample manipulator 104 may perform this operation in any number of suitable ways. Textile sample data can be recorded such as, but not limited to: whether combustion occurred; combustion or ignition temperature; spectral data related to the combustion; gas chromatographic data related to gasses released as a result of combustion; degree of melting, vaporization, or carbonization; and so on.

In another embodiment, the textile sample manipulator 104 may be configured to expose the textile sample to light or sound. The textile sample manipulator 104 may perform this operation in any number of suitable ways. Textile sample data can be recorded such as, but not limited to: reflectivity, absorption, or transmittance of sound and/or light; spectral data related to reflectivity or transmittance of light; and so on.

In another embodiment, the textile sample manipulator 104 may be configured to twist the textile sample to a particular angle, with a particular amount of torque, or until the sample rips. The textile sample manipulator 104 may perform this operation in any number of suitable ways. Textile sample data can be recorded such as, but not limited to: angle or torque at which a rip begins, location of a rip, axial retraction force of the sample, amount of change in color of the sample during the twist, radius or diameter of the material at a geometric center of the twist, and so on.

Once one or more textile sample data is obtained by the textile sample manipulator 104, the textile sample data may be received by the textile type classifier 106. The textile type classifier 106 can be implemented in any number of suitable ways, but in a typical embodiment, the textile type classifier 106 includes, or is in communication with, one or more of a processor, a memory, a power supply, one or more sensors, one or more communication interfaces, one or more data connectors, one or more power connectors, one or more input/output devices (such as a speaker, a rotary input device, a microphone, an on/off button), and so on.

The textile type classifier 106 is configured to compare the textile sample data to one or more entries in the textile characteristic database 108 in order to determine whether the textile sample data can be correlated to a textile type.

For example, in one embodiment the textile type classifier 106 receives textile sample data related to an elasticity of the textile sample. The textile type classifier 106 can compare the textile sample data to elasticity data contained in the textile characteristic database 108. The textile type classifier 106 may determine, in this example, that the textile sample data is within one standard deviation of a known elasticity of cotton and within two standard deviations of a known elasticity of denim. In this example, the textile type classifier 106 may classify the textile sample, based on the textile sample data, as denim and/or cotton.

In another example, the textile type classifier 106 receives textile sample data related to an elasticity of the textile sample along a first axis and along a second axis. The elasticity of the textile sample along the first axis may be different than the elasticity of the textile sample along the second axis. The textile type classifier 106 may determine, in this example, that the textile sample data related to the first axis is within one standard deviation of a known elasticity of nylon and that the textile sample data relate to the second axis is within one standard deviation of a known elasticity of rayon. In this example, the textile type classifier 106 may classify the textile sample, based on the textile sample data, as a rayon-nylon blend (e.g., rayon weave and nylon weft).

In yet another example, the textile type classifier 106 receives textile sample data related to the elasticity of the textile sample along one axis and textile sample data related to color of the textile sample. The textile type classifier 106 may determine, in this example, that the textile sample data is within one standard deviation of a known elasticity of wool and that the textile sample data is within one standard deviation of a known color of flannel. In this example, the textile type classifier 106 may classify the textile sample, based on the textile sample data, as flannel.

In yet another example, the textile type classifier 106 receives textile sample data related to the ignition temperature of the textile sample. The textile type classifier 106 may determine, in this example, that the textile sample data is within one standard deviation of a known ignition temperature of bamboo. In this example, the textile type classifier 106 may classify the textile sample, based on the textile sample data, as bamboo fiber.

In yet another example, the textile type classifier 106 receives textile sample data related to the combustion spectrum of the textile sample. The textile type classifier 106 may determine, in this example, that the textile sample data is within one standard deviation of a known combustion spectrum of acetate. In this example, the textile type classifier 106 may classify the textile sample, based on the textile sample data, as acetate.

In yet another example, the textile type classifier 106 receives textile sample data related to the dissolution time of the textile sample when the textile sample is placed in acetone. The textile type classifier 106 may determine, in this example, that the textile sample data is within one standard deviation of a known dissolution time of rayon acetate. In this example, the textile type classifier 106 may classify the textile sample, based on the textile sample data, as rayon acetate.

In yet another example, the textile type classifier 106 receives textile sample data related to the porosity or resistance to gas-flow exhibited by the textile sample when pressurized gas (e.g., air, nitrogen, and so on) is forced through the textile sample. The textile type classifier 106 may determine, in this example, that the textile sample data is within one standard deviation of a known gas-flow resistance of tight linen. In this example, the textile type classifier 106 may classify the textile sample, based on the textile sample data, as tight linen.

In yet another example, the textile type classifier 106 receives textile sample data related to the recovery time of the textile sample when the textile sample is stretched and released. The textile type classifier 106 may determine, in this example, that the textile sample data is within one standard deviation of a known recovery time of elastic. In this example, the textile type classifier 106 may classify the textile sample, based on the textile sample data, as elastic.

In further examples, the textile type classifier 106 may receive textile sample data related to any number of textile characteristics of the textile sample including, but not limited to: elasticity properties, acoustic properties, electrostatic properties, combustion properties, optical properties, chemical properties, dissolution properties, and so on.

The textile type classifier 106 may use any number of suitable statistical methods to determine whether textile sample data corresponds to a particular textile type or more than one textile type. In some cases, the statistical method may be a standard deviation comparison, such as described above, but this may not be required. One of skill in the art will appreciate that any number of suitable matching and/or statistical similarity methods may be used.

In further examples, the textile type classifier 106 may accept input from an operator. For example, an operator can input a source of the textile sample. Based on the source of the sample, the textile type classifier 106 may narrow the potential textile types that may be associated with the textile sample. For example, an operator may input to the textile type classifier 106 that the textile sample originated at a commercial linen fabricator. In this example, the textile type classifier 106 may determine that that the textile sample may be one Irish linen, sheeting linen, patterned linen, loose weave linen, tight weave linen, toweling linen, and so on.

The embodiment depicted in FIG. 1 is provided to facilitate a general understanding of potential implementations of a textile identification system such as described herein. As such, it may be appreciated that the examples provided above are not intended to be limiting. In other words, a textile identification system such as described herein may be implemented in any number of suitable ways including all or some of the components, modules, subsystems, sensors referenced above.

Figure 2A:
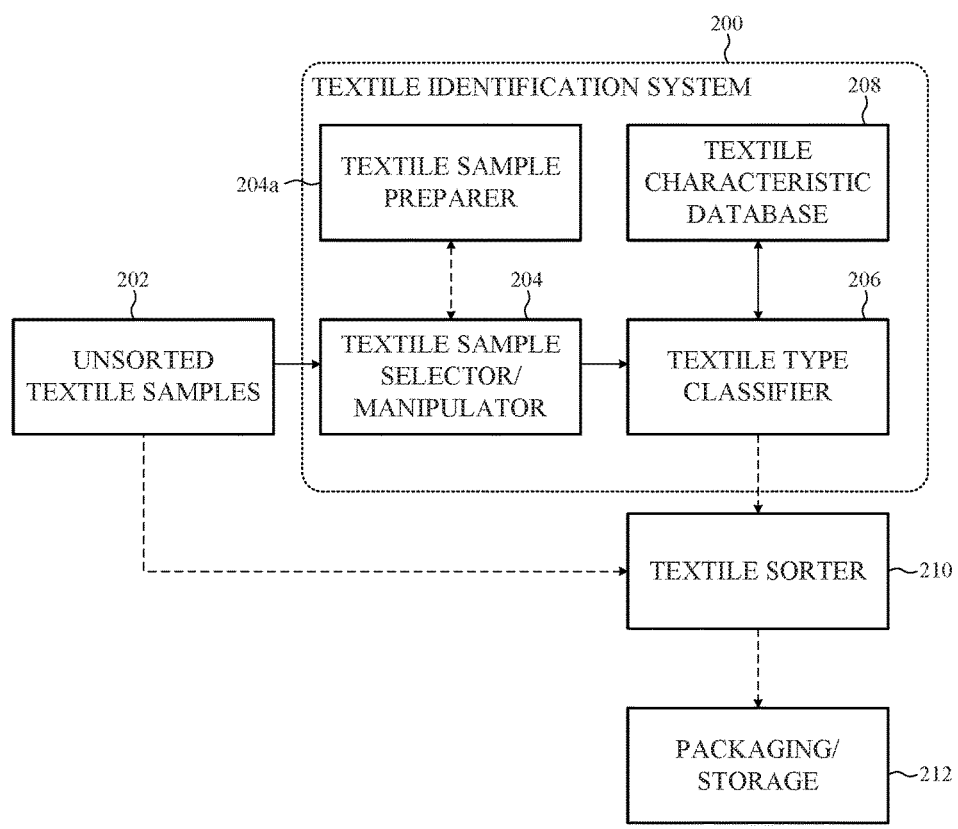
FIG. 2A depicts a simplified system diagram of a textile sorting system that may operate in accordance with methods described herein.

FIG. 2A depicts a simplified system diagram of a textile sorting system that may operate in accordance with methods described herein. The textile sorting system includes a textile identification system. The textile identification system 200 can select a textile sample form a source of unsorted textile samples 202. The textile identification system 200 can include a textile sample selector/manipulator 204 in order to make (or receive) the selection.

In some embodiments, the textile identification system 200 includes a textile sample preparer 204a. The textile sample preparer 204a may be configured to prepare the textile sample selected by or received by the textile sample selector/manipulator 204. For example, the textile sample preparer 204a may be configured to, without limitation: clean the textile sample with detergent; saturate the textile sample in a chemical such as water, acetone, bleach, and so on; air blast the textile sample; cut the textile sample to a particular size or shape; trim one or more edges of the textile sample; attach an identifier tag to the textile sample, such as a radio frequency identification tag; print or adhere an identification number to the textile sample, such as a bar code, a quick responds code, a serial number; and so on. In some cases, the textile sample preparer 204a may be configured to divide the textile sample. For example, a textile sample may be layered with different materials; the textile sample prepare 204a may delaminate and/or de-layer the textile sample. The separated components may each be passed to the textile sample selector/manipulator 204. In another example, a textile sample may include an elastic waistband; the textile sample preparer 204 may separate the waistband, passing the waistband to the textile sample selector/manipulator 204 sparely from the remainder of the textile sample. In another example, a textile sample may include an interior lining; the textile sample preparer 204 may separate the interior lining, passing the interior lining to the textile sample selector/manipulator 204 sparely from the remainder of the textile sample.

Once the textile sample is received by the textile sample selector/manipulator 204 (and optionally prepared or processed by the textile sample preparer 204a), the textile sample selector/manipulator 204 can manipulate the textile sample in order to obtain textile sample data. As noted with respect to other embodiments described herein, the sample may be manipulated in any number of suitable ways including but not limited to: stretching, twisting, weighing, photographing, combusting, and so on. As a result of the manipulation, textile sample data is collected; textile sample data is thereafter passed to a textile type classifier 206.

The textile type classifier 206 may be implemented in any number of suitable ways. In many embodiments, the textile type classifier 206 is coupled to a textile characteristic database 208. The textile type classifier 206 can compare the textile sample data to information contained in the textile characteristic database 208 in order to classify the textile sample as a particular textile type or as one or more textile types.

Figure 2B:
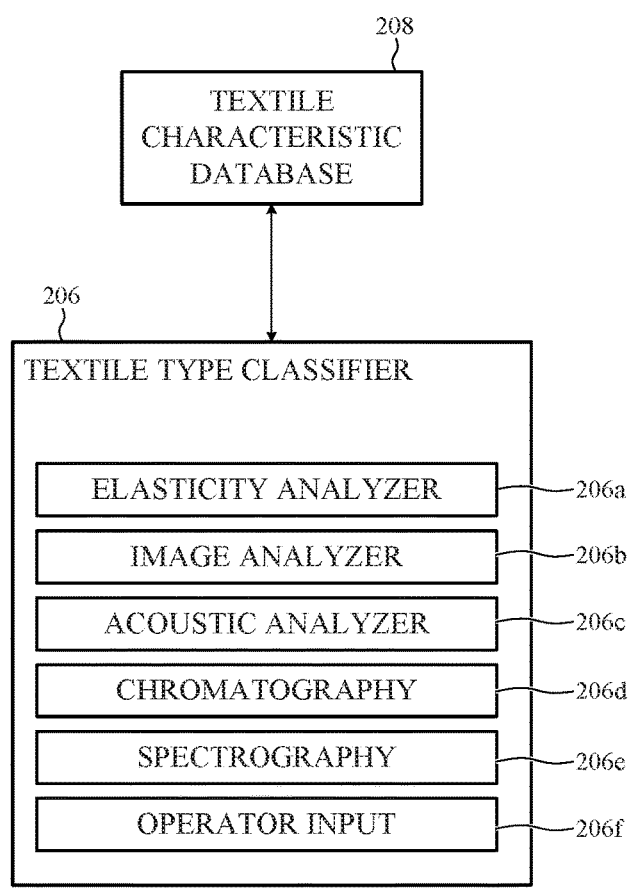
FIG. 2B depicts a simplified system diagram of a textile type classifier that may be used with the textile sorting system of FIG. 2A.

One example implementation of the textile type classifier 206 is depicted in FIG. 2B. The textile type classifier 206 can include subsystems such as, but not limited to: an elasticity analyzer 206a, an image analyzer 206b, an acoustic property analyzer 206c, a chromatography analyzer 206d, a spectrographic analyzer 206e, and/or a means for accepting and receiving operating input 206f. In other cases, the textile type classifier 206 can include additional or fewer components or subsystems. In some cases, the textile type classifier 206 is a single computing system. In other cases, the textile type classifier 206 is a network of computing systems, each of which may include subsystems such as shown in FIG. 2B. It may be appreciated that the textile type classifier 206 can be implemented in any number of suitable ways.

Returning to FIG. 2A, it may be appreciated that in some embodiments, the textile sample data received by the textile type classifier 206 may be insufficient, on its own, to determine a particular textile type with a particular degree of statistical confidence. In these embodiments, the textile type classifier 206 may communicate to the textile sample selector/manipulator 204 that the textile sample should be further manipulated in order to obtain additional textile sample data.

In these embodiments, the textile sample selector/manipulator 204 and the textile type classifier 206 may communicate in real time; the textile sample selector/manipulator 204 may communicate textile sample data to the textile type classifier 206 as different manipulation operations are performed. Once enough textile sample data is obtained, the textile type classifier 206 can instruct the textile sample selector/manipulator 206 to cease manipulating the textile sample. In many cases, the textile sample selector/manipulator 206 perform manipulation operations in an order based on the time required to perform the operations; slower manipulation operations are deferred until after faster operations are completed. For example, the textile sample selector/manipulator 206 may begin by photographing the textile sample, passing the image data immediately to the textile type classifier 206. In some cases, the textile type classifier 206 may be able to determine a textile type based only on the image data, whereas in other cases, image data may be insufficient. In the case that image data is insufficient on its own to determine a textile type, the textile sample selector/manipulator 206 may continue by stretching the textile sample to obtain textile sample data related to elasticity. In some cases, the textile type classifier 206 may be able to determine a textile type based on the image data and the elasticity data, whereas in other cases, the combination of image data and elasticity data may be insufficient. In the case that the combined image data and elasticity data is insufficient on its own to determine a textile type, the textile sample selector/manipulator 206 may continue by stretching the textile sample along another axis to obtain textile sample data related to elasticity along two axes. In some cases, the textile type classifier 206 may be able to determine a textile type based on the image data and the multi-axis elasticity data, whereas in other cases, the combination image data and elasticity data may be insufficient.

In one example, the textile sample selector/manipulator 206 may perform operations in an order such as: photographing the textile sample, weighing the textile sample, determining a length and/or width of the textile sample, determining a color of the textile sample, determining an elastic property of the textile sample along a first axis, determining an elastic property of the textile sample along a second axis, determining an elastic property of the textile sample along a third axis, determining a combustion or ignition property of the textile sample, performing gas chromatography operation on gases emitted during combustion of the textile sample, properties related to dissolving the textile sample in a solvent, properties related to bleaching the textile sample, properties related to x-ray spectroscopy of the textile sample. As may be appreciated, these operations are provided in an order generally related to speed with which such operations may be performed; depending on equipment and/or implementation choices for a particular embodiment, a different order that that presented above may be more appropriate. In many cases, additional or fewer operations may be performed by the textile identification system 200.

As a result of the ordering (or staging) of different operations of the textile sample selector/manipulator 206 based on the speed with which those operations may be performed, a large number of textile samples may be classified in a time-efficient manner; easily classifiable textile samples may be classified quickly and difficult-to-classify materials may be classified accurately. In other words, the average time to classify an arbitrary set of textile samples may be reduced in comparison to traditional classification methods that either employ high-speed and inaccurate classification methods (e.g., photographic or reflective identification only) or employ low-speed and high-accuracy classification methods (e.g., x-ray spectroscopy or near infrared spectroscopy).

Once the textile type classifier 206 has determined one or more textile types of the textile sample, the textile type may be communicated to a textile sorter 210. The textile sorter 210 may be implemented in any number of suitable ways. In some cases, the textile sorter 210 is a conveyor sorter or a pick and place machine. The textile sorter 210 is configured to sort the textile sample, and any other samples that are known to be related to or associated with the textile sample, into groups based on the one or more textile types. Once sorted, groups of like materials may be packaged, prepared, or otherwise processed for reuse, repurposing, or recycling by a packaging or storage system 212. In other cases, the packaging or storage system 212 can process the group for efficient and responsible disposal by incineration, disintegration, biodegradation, or any other suitable textile type-specific or textile type-appropriate disposal method.

The foregoing description of the embodiments depicted in FIGS. 1 and 2A-2B and various alternatives and variations, are presented, generally, for purposes of explanation, and to facilitate a general understanding of possible textile identification and/or sorting embodiments disclosed herein. However, it will be apparent to one skilled in the art that some of the specific details presented herein may not be required in order to practice a particular described embodiment, or an equivalent thereof. In particular, it may be appreciated that a textile identification and/or sorting system such as described above may be operated in a number of ways, each of which may facilitate identification and/or classification of one or more textile samples.

Generally and broadly, FIGS. 3-10 are provided to facilitate a general understanding various example methods of operating a textile identification system such as described herein.

As noted with respect to other embodiments, a textile identification system can be implemented in any number of suitable ways. For example, a textile identification system can include, or can be placed in communication with, one or more computing devices in wired or wireless communication with one or more databases, external computing devices, conveyor or transport systems, sorting systems, camera systems, audio systems, chemical analysis systems, spectrometry systems, chromatography systems, gas venting and/or collection systems, and so on. In further embodiments, a textile identification system can include, or can be placed in communication with, any number of suitable sensors that may be used to determine one or more textile characteristics. Such sensors can include, but are not limited to, acoustic sensors, light sensors, camera sensors, infrared sensors, ultraviolet sensors, strain sensors, force sensors, chemical sensors, and so on. In still further examples, a textile identification system can be configured in any other suitable or implementation-specific manner.

Figure 3:
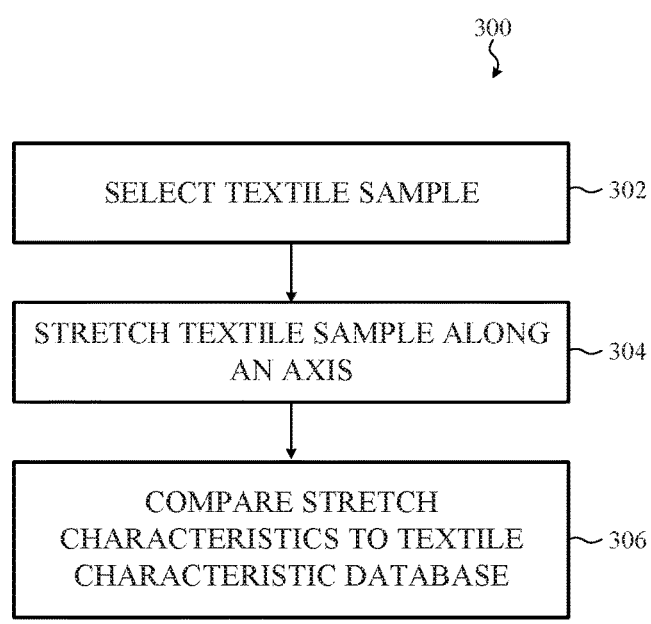
FIG. 3 is a flow chart that depicts example operations of a method of obtaining textile sample data related to a textile characteristic of a textile sample by stretching the textile sample along or about an axis.

FIG. 3 is a flow chart that depicts example operations of a method of obtaining textile sample data related to a textile characteristic of a textile sample by stretching the textile sample along or about an axis. In some embodiments the method 300 can be performed, in whole or in part, by a textile identification system such as the textile identification system 200 depicted in FIGS. 2A-2B. In other cases, the method 300 can be performed in whole or in part by a fixed or portable computing system such as an industrial control system, a desktop computing system, a laptop computing system, or any other suitable computing system.

The method 300 begins at operation 302 in which a textile sample is selected. In some cases, the textile sample is received from an operator of a textile identification system. In other cases, the textile sample is selected by a textile sample selector. In some examples, the sample is selected from a group of similar samples, although this may not be required.

Next, at operation 304, the textile sample is stretched. The sample may be stretched along an axis parallel to a length or width of the sample. In other cases, the sample is stretched along another axis, such an axis defined between opposite corners of a rectangular textile sample.

The sample may be stretched with any suitable mechanism or combination of mechanisms. In one example, the sample may be grasped by a vice and a pulling arm. The pulling arm may be configured to exert a fixed or variable amount of force to stretch the sample. In other cases, the sample may be grasped by two different pulling arms which may be configured to exert a fixed or variable amount of force to stretch the sample.

Next at operation 306, characteristics of the stretch may be compared to a textile characteristic database. Characteristics of the stretch may be any textile sample data collected prior to, during, or after the stretch operation is performed. For example, characteristics of the stretch may be a color of the textile sample before, during, or after the stretch. In other cases, characteristics of the stretch may be related to elasticity of the sample before, during, or after the stretch (e.g., recovery, modulus of elasticity, necking point, strain hardening point, fracture strengthening point, and so on). In other embodiments, characteristics of the stretch can be related to other properties or characteristics of the textile sample.

Figure 4:
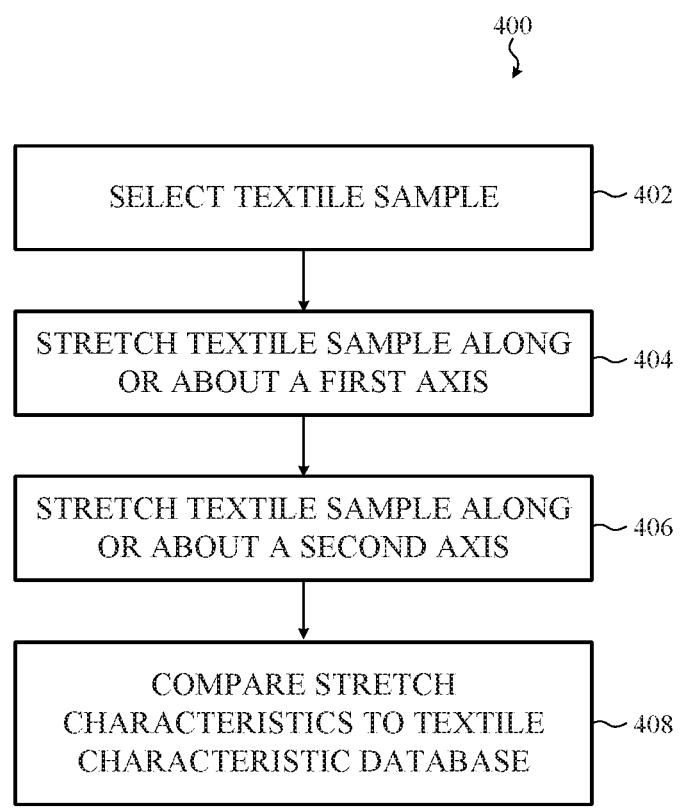
FIG. 4 is a flow chart that depicts example operations of another method of obtaining textile sample data related to a textile characteristic of a textile sample by stretching the textile sample along or about a first and second axis.

FIG. 4 is a flow chart that depicts example operations of another method of obtaining textile sample data related to a textile characteristic of a textile sample by stretching the textile sample along or about a first and second axis. As with other embodiments described herein, the method 400 can be performed, in whole or in part, by a textile identification system, such as the textile identification system 200 depicted in FIGS. 2A-2B. In other cases, the method 400 can be performed in whole or in part by a fixed or portable computing system such as an industrial control system, a desktop computing system, a laptop computing system, or any other suitable computing system.

The method 400 begins at operation 402 in which a textile sample is selected. In some cases, the textile sample is received from an operator of a textile identification system. In other cases, the textile sample is selected by a textile sample selector. In some examples, the sample is selected from a group of similar samples, although this may not be required.

Next, at operation 404, the textile sample is stretched along a first axis. The sample may be stretched along an axis parallel to a length or width of the sample. In other cases, the sample is stretched along another axis, such an axis defined between opposite corners of a rectangular textile sample.

As noted with respect to other embodiments described herein, the sample may be stretched with any suitable mechanism or combination of mechanisms. In one example, the sample may be grasped by a vice and a pulling arm. The pulling arm may be configured to exert a fixed or variable amount of force to stretch the sample. In other cases, the sample may be grasped by two different pulling arms which may be configured to exert a fixed or variable amount of force to stretch the sample.

Next, at operation 406, the textile sample is stretched along a second axis. As with the first axis pulling operation, the sample may be stretched along the second axis parallel to a length or width of the sample. In some cases, the second axis is perpendicular to the first axis. The amount of force of the second stretch operation may be equal to or different from the stretch operation 404.

Finally at operation 408, characteristics of the stretch relative to the first axis and characteristics of the stretch relative to the second axis may be compared to entries in a textile characteristic database. Characteristics of the stretch may be any textile sample data collected prior to, during, or after either stretch operation is performed. For example, characteristics of the stretch may be a color of the textile sample before, during, or after the stretch operations. In other cases, characteristics of the stretches may be related to elasticity of the sample before, during, or after the stretch (e.g., recovery, modulus of elasticity, necking point, strain hardening point, fracture strengthening point, and so on). In other embodiments, characteristics of the stretch can be related to other properties or characteristics of the textile sample.

Figure 5:
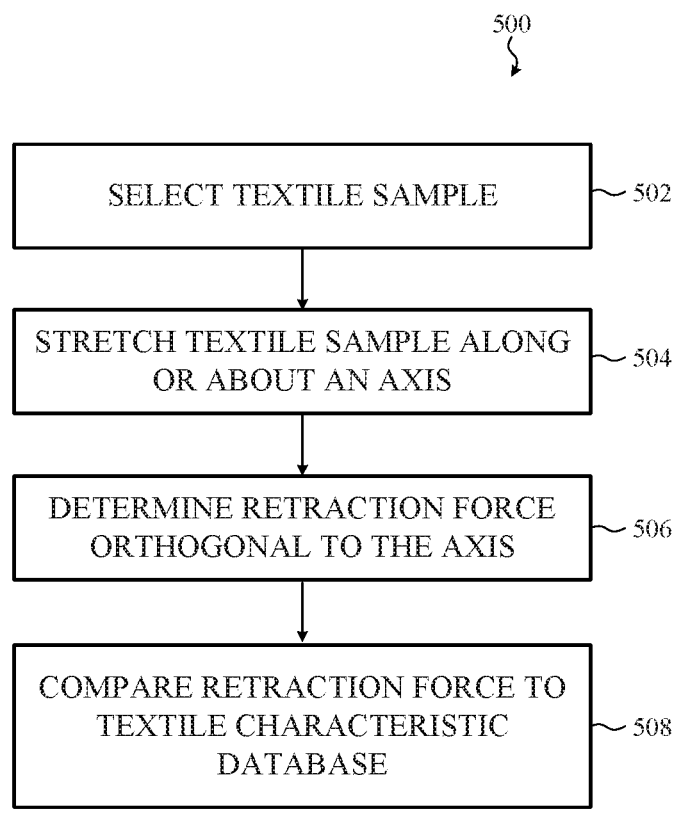
FIG. 5 is a flow chart that depicts example operations of another method of obtaining textile sample data related to a textile characteristic of a textile sample by measuring retraction of the sample when the sample is stretched along an axis.

FIG. 5 is a flow chart that depicts example operations of another method of obtaining textile sample data related to a textile characteristic of a textile sample by measuring retraction of the sample when the sample is stretched along an axis. As with other embodiments described herein, the method 500 can be performed, in whole or in part, by a textile identification system, such as the textile identification system 200 depicted in FIGS. 2A-2B. In the alternative, the method 500 can be performed in whole or in part by a fixed or portable computing system such as an industrial control system, a desktop computing system, a laptop computing system, or any other suitable computing system.

The method 500 begins at operation 502 in which a textile sample is selected. In some cases, the textile sample is received from an operator of a textile identification system. In other cases, the textile sample is selected by a textile sample selector. In some examples, the sample is selected from a group of similar samples, although this may not be required.

Next, at operation 504, the textile sample is stretched. As with other embodiments described herein, the sample may be stretched along an axis parallel to a length or width of the sample. In other cases, the sample is stretched along another axis, such an axis defined between opposite corners of a rectangular textile sample.

As noted above with respect to the embodiments described in reference to FIGS. 3 and 4, the textile sample may be stretched with any suitable mechanism or combination of mechanisms. In one example, the sample may be grasped by a vice and a pulling arm. The pulling arm may be configured to exert a fixed or variable amount of force to stretch the sample. In other cases, the sample may be grasped by two different pulling arms which may be configured to exert a fixed or variable amount of force to stretch the sample.

Next, at operation 506 an amount or magnitude of retraction force can be measured. The retraction force can be measured along an axis that is perpendicular to the stretch axis. For example, if the stretch axis is defined between opposite corners of a rectangular textile sample, the retraction force may be measured between the other corners of the rectangular textile sample. In the case that the stretch axis is parallel to a length of the textile sample, the retraction force can be measured along an axis parallel to a width of the textile sample.

Finally at operation 508, characteristics of the stretch relative to the stretch axis and characteristics of the retraction may be compared to entries in a textile characteristic database. Characteristics of the stretch or retraction may be any textile sample data collected prior to, during, or after either stretch operation is performed. For example, characteristics of the stretch may be a color of the textile sample before, during, or after the stretch operations. In other cases, characteristics of the stretch or retraction may be related to elasticity of the sample before, during, or after the stretch (e.g., recovery, modulus of elasticity, necking point, strain hardening point, fracture strengthening point, and so on). In other embodiments, characteristics of the stretch can be related to other properties or characteristics of the textile sample.

Figure 6:
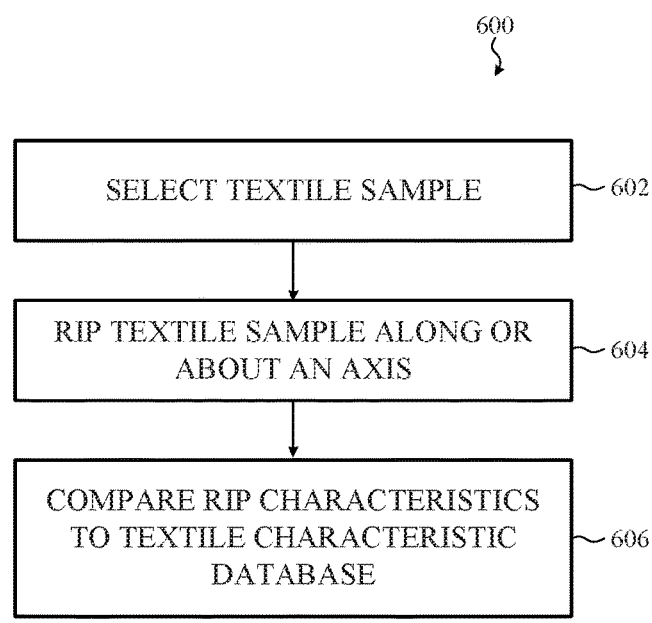
FIG. 6 is a flow chart that depicts example operations of another method of obtaining textile sample data related to a textile characteristic of a textile sample by ripping the textile sample along or about an axis.

FIG. 6 is a flow chart that depicts example operations of another method of obtaining textile sample data related to a textile characteristic of a textile sample by ripping the textile sample along or about an axis. As with other embodiments described herein, the method 600 can be performed, in whole or in part, by a textile identification system, such as the textile identification system 200 depicted in FIGS. 2A-2B. In the alternative, the method 600 can be performed in whole or in part by a fixed or portable computing system such as an industrial control system, a desktop computing system, a laptop computing system, or any other suitable computing system.

The method 600 begins at operation 602 in which a textile sample is selected. In some cases, the textile sample is received from an operator of a textile identification system. In other cases, the textile sample is selected by a textile sample selector. In some examples, the sample is selected from a group of similar samples, although this may not be required.

Next, at operation 604, the textile sample is ripped. The sample may be ripped along an axis parallel to a length or width of the sample. In other cases, the sample is ripped along another axis, such an axis defined between opposite corners of a rectangular textile sample.

The sample may be ripped with any suitable mechanism or combination of mechanisms. In one example, the sample may be grasped by a vice and a pulling arm. The pulling arm may be configured to exert a fixed or variable amount of force to rip the sample. In other cases, the sample may be grasped by two different pulling arms which may be configured to exert a fixed or variable amount of force to rip the sample.

Next at operation 606, characteristics of the rip may be compared to a textile characteristic database. Characteristics of the rip may be any textile sample data collected prior to, during, or after the rip operation is performed. For example, characteristics of the rip may be a color of the textile sample before, during, or after the rip. In other cases, characteristics of the rip may be related to elasticity of the sample before, during, or after the rip (e.g., recovery, modulus of elasticity, necking point, strain hardening point, fracture strengthening point, and so on). In other embodiments, characteristics of the rip can be related to other properties or characteristics of the textile sample.

Figure 7:
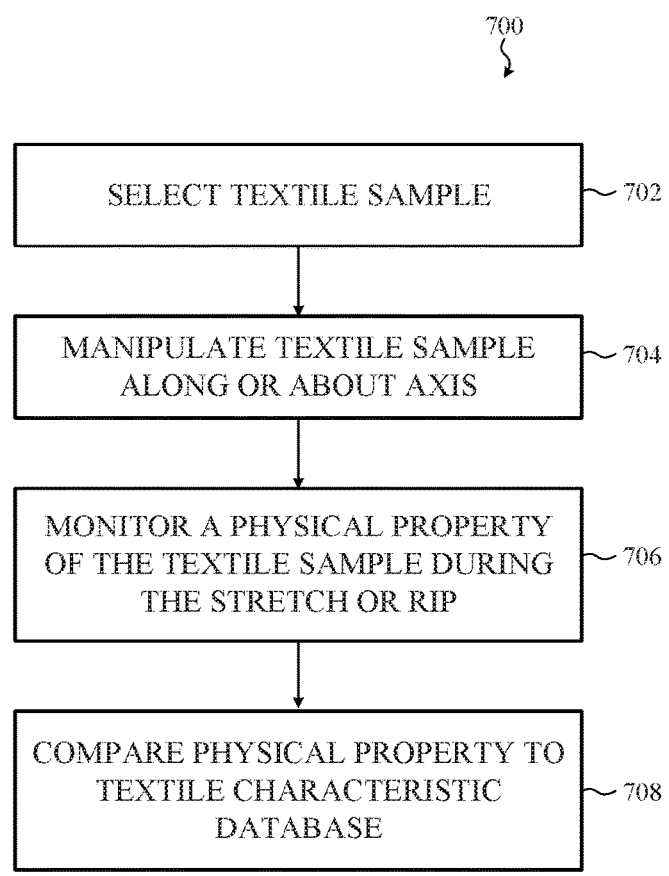
FIG. 7 is a flow chart that depicts example operations of another method of obtaining textile sample data related to a textile characteristic by manipulating a textile sample.

FIG. 7 is a flow chart that depicts example operations of another method of obtaining textile sample data related to a textile characteristic by manipulating a textile sample. As with other embodiments described herein, the method 700 can be performed, in whole or in part, by a textile identification system, such as the textile identification system 200 depicted in FIGS. 2A-2B. In the alternative, the method 700 can be performed in whole or in part by a fixed or portable computing system such as an industrial control system, a desktop computing system, a laptop computing system, or any other suitable computing system.

The method 700 begins at operation 702 in which a textile sample is selected. In some cases, the textile sample is received from an operator of a textile identification system. In other cases, the textile sample is selected by a textile sample selector. In some examples, the sample is selected from a group of similar samples, although this may not be required.

Next, at operation 704, the textile sample is manipulated in a manner that may cause the sample to stretch and/or rip. As with other embodiments described herein, the sample may be stretched along an axis parallel to a length or width of the sample. In other cases, the sample is stretched along another axis, such an axis defined between opposite corners of a rectangular textile sample.

As noted above with respect to the embodiments described in reference to FIGS. 3 and 4, the textile sample may be stretched, strained, or ripped with any suitable mechanism or combination of mechanisms. In one example, the sample may be grasped by a vice and a pulling arm. The pulling arm may be configured to exert a fixed or variable amount of force to stretch the sample. In other cases, the sample may be grasped by two different pulling arms which may be configured to exert a fixed or variable amount of force to stretch the sample. In other cases, the sample may be twisted about an axis. The sample may be twisted until the sample rips, the sample may be twisted to a particular torque, the sample may be twisted to a particular angle, and so on.

Next, at operation 706, one or more physical properties of the sample may be monitored during the manipulation performed at operation 704. A monitored physical property can include, but may not be limited to: width of the sample, length of the sample, radius of a twisted portion of the sample, color of the sample, acoustic output from the sample during a stretch or twist operation and so on. In other cases, the temperature of the sample may be monitored.

Finally at operation 708, characteristics of the stretch relative to the stretch axis and characteristics of the retraction may be compared to entries in a textile characteristic database. Characteristics of the stretch or retraction may be any textile sample data collected prior to, during, or after either stretch operation is performed. For example, characteristics of the stretch may be a color of the textile sample before, during, or after the stretch operations. In other cases, characteristics of the stretch or retraction may be related to elasticity of the sample before, during, or after the stretch (e.g., recovery, modulus of elasticity, necking point, strain hardening point, fracture strengthening point, and so on). In other embodiments, characteristics of the stretch can be related to other properties or characteristics of the textile sample.

The foregoing description of the embodiments depicted in FIGS. 3-7 and various alternatives and variations, are presented, generally, for purposes of explanation, and to facilitate a general understanding of possible methods of operating a textile identification and/or sorting embodiments disclosed herein. However, it will be apparent to one skilled in the art that some of the specific details presented herein may not be required in order to practice a particular described embodiment, or an equivalent thereof. In particular, it may be appreciated that a textile identification and/or sorting system such as described above may be operated in a number of ways, each of which may facilitate identification and/or classification of one or more textile samples.

Figure 8:
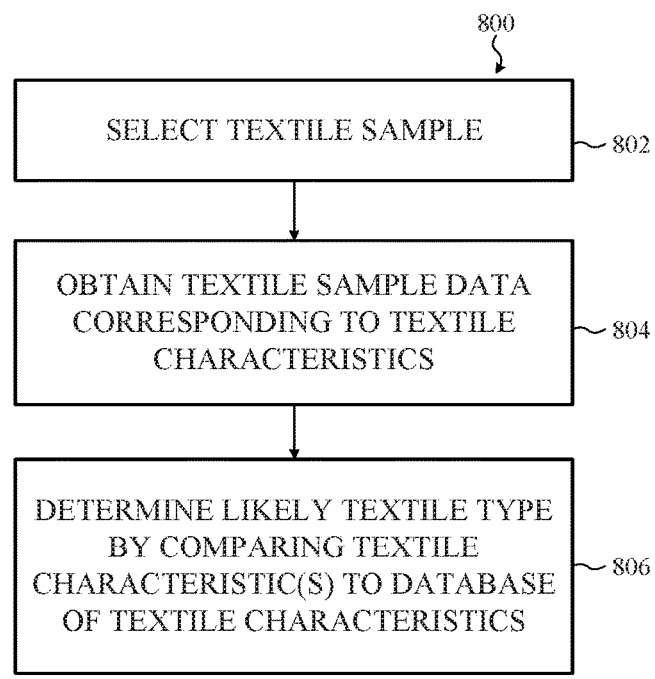
FIG. 8 is a flow chart that depicts example operations of a method of classifying a textile sample based on textile sample data that corresponds to one or more textile characteristics.

More generally and broadly, the operation of a textile identification system such as described herein selects a textile sample, obtains textile sample data corresponding to one or more textile characteristics of the textile sample, and then determines whether the textile sample data can be used to classify the textile sample as one or more textile types. FIG. 8 depicts such a method. The method 800 begins at operation 802 in which a textile sample is selected. Next at operation 804, textile sample data is collected. As noted with respect to other embodiments described herein, textile sample data can be any data related to any physical or chemical property of the textile sample (or any change in such a property) such as, but not limited to: length, width, thickness, weight, weave pattern, chemical makeup, magnetic properties, electrical properties, chemical properties and so on.

Figure 9:
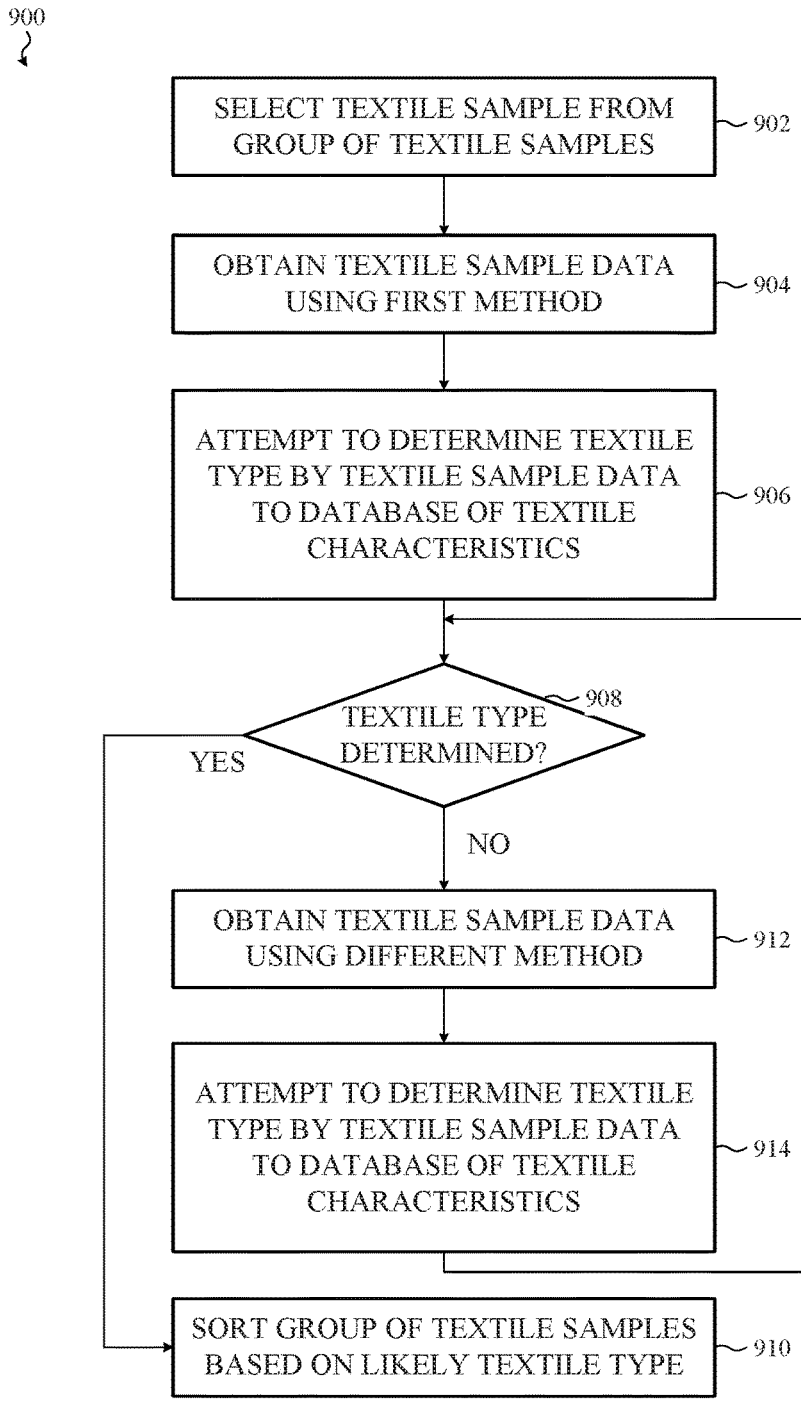
FIG. 9 is a flow chart that depicts example operations of another method of classifying a textile sample based on textile sample data that corresponds to one or more textile characteristics.

FIG. 9 is a flow chart that depicts example operations of another method of classifying a textile sample based on textile sample data that corresponds to one or more textile characteristics. As with other embodiments described herein, the method 900 can be performed, in whole or in part, by a textile identification system, such as the textile identification system 200 depicted in FIGS. 2A-2B. In the alternative, the method 900 can be performed in whole or in part by a fixed or portable computing system such as an industrial control system, a desktop computing system, a laptop computing system, or any other suitable computing system.

The method 900 begins at operation 902 in which a textile sample is selected from a group of textile samples. Next at operation 904, textile sample data can be obtained using a first method. Next at operation 906, an attempt at matching the textile sample data to a particular textile type is made. Next, at operation 908, if a textile type is determined, the method continues to operation 910 in which the group of textile samples are sorted and classified based on the textile type. Alternatively, at operation 908, if a textile type was not determined, the method can continue to operation 912 in which, textile sample data can be obtained using a different method. In many cases, the second method may be more accurate than the first method. Next at operation 914, an attempt at matching the textile sample data to a particular textile type is made. The method continues to operation 910 at which the group of textile samples are sorted and classified based on the textile type. Alternatively, the method may return to operation 908.

Figure 10:
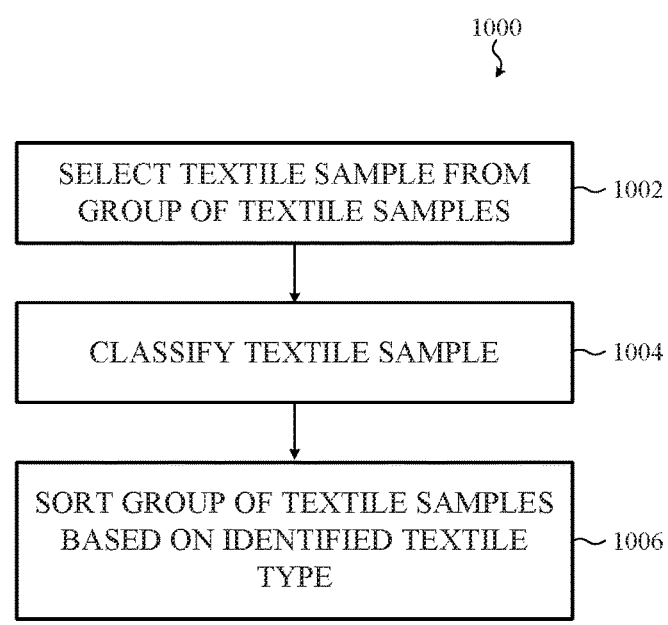
FIG. 10 is a flow chart that depicts example operations of a method of sorting textile samples.

FIG. 10 is a flow chart that depicts example operations of a method of sorting textile samples. As with other embodiments described herein, the method 1000 can be performed, in whole or in part, by a textile identification system, such as the textile identification system 200 depicted in FIGS. 2A-2B. The method 1000 begins at operation 1002 in which a textile sample is selected from a group of textile samples. At operation 1004, the textile sample is classified as a particular textile type. Lastly, at operation 1006, the entire group is classified and sorted based on the classification of the single textile sample selected at operation 1002.

One may appreciate that although many embodiments are disclosed above, that the operations and steps presented with respect to methods and techniques described herein are meant as exemplary and accordingly are not exhaustive. One may further appreciate that an alternate step order or fewer or additional steps may be implemented in particular embodiments.

Although the disclosure above is described in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the embodiments of the invention, whether or not such embodiments are described and whether or not such features are presented as being a part of a described embodiment. Thus, the breadth and scope of the present invention should not be limited by any of the above-described exemplary embodiments but is instead defined by the claims herein presented.

What is claimed is:

1. A method of classifying a textile sample of an unknown type for recycling, the method comprising:
   selecting a textile sample of an unknown textile type:
   obtaining textile sample data related to a textile characteristic of the textile sample by:
      performing a first manipulation of the textile sample to change a first dimension of the textile sample; and
      performing a second manipulation of the textile sample to change a second dimension of the textile sample;
   comparing the textile sample data to a database of textile characteristics;
   determining a set of probable textile types based on the comparison;
   selecting at least one probable textile type from the set of probable textile types;
   classifying the textile sample as the at least one probable textile type; and
   sorting the textile sample for recycling based on the classification.

2. The method of claim 1, further comprising sending a signal to a sorting mechanism based on the classification.

3. The method of claim 2, wherein sorting the textile sample based on the classification comprises delivering the textile sample to the sorting mechanism.

4. The method of claim 1, wherein:
   the textile sample is a member of a set of textile samples of unknown textile types; and
   the method further comprises, prior to obtaining the textile characteristic:
      selecting the textile sample from the set of textile samples of unknown textile types based on a preliminary textile type assessment; and
      separating the textile sample from the set of textile samples of unknown textile types.

5. The method of claim 4, wherein the preliminary textile type assessment is based on a known origin of the set of unknown textile samples.

6. The method of claim 1, wherein the textile characteristic comprises an elastic deformation property of the textile sample.

7. The method of claim 1, wherein the textile characteristic comprises an acoustic property of the textile sample.

8. The method of claim 1, wherein the textile characteristic comprises an optical property of the textile sample.

9. The method of claim 1, wherein the textile characteristic comprises a liquid absorption property of the textile sample.

10. The method of claim 1, wherein the textile characteristic comprises at least one of:
- a torsion property of the textile sample;
- a compressive property of the textile sample;
- a plastic deformation property of the textile sample;
- a yield strength property of the textile sample;
- a fracture strength of the textile sample;
- a necking strain range associated with the textile sample; or
- a strain hardening range associated with the textile sample.

11. The method of claim 1, wherein manipulating the textile sample comprises at least one of:
- positioning the textile sample in a stretching tool; or
- positioning the textile sample in a ripping tool.

12. A method of classifying a textile sample set for recycling, the method comprising:
- selecting a textile sample of an unknown textile type from the textile sample set based on a predetermined minimum length of the textile sample;
- elongating the textile sample along an axis;
- detecting changes in an elongation property of the textile sample during the elongation of the textile sample;
- selecting at least one probable textile type from a set of probable textile types based on the detected changes in the elongation property;
- classifying the textile sample set as of the at least one probable textile type; and
- sorting the textile sample set for recycling according to the classification of the textile sample.

13. The method of claim 12, wherein the operation of obtaining the elongation property of the textile sample comprises:
- obtaining a first measurement of a length of the textile sample along the axis;
- stretching the textile sample along the axis until the textile sample reaches a yield point;
- releasing the textile sample;
- obtaining a second measurement of the length of the textile sample along the axis; and
- determining a difference between the first measurement and the second measurement.

14. The method of claim 13, wherein:
- the axis is a first axis; and
- the operation of detecting changes in the elongation property of the textile sample comprises:
  - stretching the textile sample along the first axis to determine a first Young's modulus of the textile sample; and
  - stretching the textile sample along a second axis orthogonal to the first axis to determine a second Young's modulus of the textile sample.

15. The method of claim 12, wherein the operation of detecting changes in the elongation property of the textile sample comprises stretching the textile sample along the axis to determine an amount of force required to tear the textile sample.

16. The method of claim 12, wherein the operation of detecting changes in the elongation property of the textile sample comprises twisting the textile sample about the axis until the textile sample rips.

17. The method of claim 12, wherein the operation of detecting changes in the elongation property of the textile sample comprises:
- twisting the textile sample about the axis to form a twisted fabric sample; and
- stretching the twisted fabric sample along the axis to determine an amount of force required to tear the twisted fabric sample.

18. The method of claim 12, wherein the operation of detecting changes in the elongation property of the textile sample comprises:
- measuring a first length of the textile sample along the axis to obtain a pre-twist length;
- twisting the textile sample about the axis to form a twisted fabric sample; and
- measuring a second length of the twisted fabric sample along the axis to obtain a post-twist length.

19. A method of classifying a textile sample set of an unknown textile type for recycling, the method comprising:
- selecting a textile sample of an unknown textile type from the textile sample set;
- destructively manipulating the textile sample;
- detecting changes in a destructive property of the textile sample during the destructive manipulate the textile sample;
- selecting at least one probable textile type from a set of probable textile types based on the detected changes in the destructive property; and
- classifying the textile sample set as of the at least one probable textile type; and
- sorting the textile sample set for recycling according to the classification of the textile sample selected from the textile sample set.

20. The method of claim 19, wherein the destructively manipulating the textile sample comprises at least one of:
- ripping the textile sample;
- stretching the textile until a rip forms; or
- increasing a temperature of the textile sample until combustion occurs.

* * * * *